(12) United States Patent
Zheng et al.

(10) Patent No.: US 9,753,430 B2
(45) Date of Patent: Sep. 5, 2017

(54) SENSOR DEVICE HAVING PLURAL RESISTANCE CHANGE SENSORS AND METHOD OF USING THE SAME

(71) Applicants: Jie Zheng, Nagoya (JP); Ryo Ito, Nagoya (JP); Kenji Kanazawa, Tsukuba (JP); Osamu Takahashi, Nagoya (JP)

(72) Inventors: Jie Zheng, Nagoya (JP); Ryo Ito, Nagoya (JP); Kenji Kanazawa, Tsukuba (JP); Osamu Takahashi, Nagoya (JP)

(73) Assignee: Brother Kogyo Kabushiki Kaisha, Nagoya-shi, Aichi-ken (JP)

( * ) Notice: Subject to any disclaimer, the term of this patent is extended or adjusted under 35 U.S.C. 154(b) by 389 days.

(21) Appl. No.: 14/224,223

(22) Filed: Mar. 25, 2014

(65) Prior Publication Data
US 2014/0283597 A1    Sep. 25, 2014

(30) Foreign Application Priority Data
Mar. 25, 2013   (JP) .................................. 2013-062089

(51) Int. Cl.
G03G 21/20       (2006.01)
G01N 27/12       (2006.01)

(52) U.S. Cl.
CPC ......... *G03G 21/203* (2013.01); *G01N 27/121* (2013.01); *G03G 2215/00084* (2013.01)

(58) Field of Classification Search
CPC ....... G03G 21/203; G03G 2215/00084; G03G 15/2078; G03G 15/5045; G01N 27/121;
(Continued)

(56) References Cited

U.S. PATENT DOCUMENTS 5,065,625 A * 11/1991 Nakagawa ........... G01N 27/045
                                                    73/29.02
5,077,566 A    12/1991 Ochiai et al.
(Continued)

FOREIGN PATENT DOCUMENTS

JP    S57-017104 A    1/1982
JP    S61-091552 A    5/1986
(Continued)

OTHER PUBLICATIONS

JP Office Action dtd Jan. 19, 2010, JP Appln. 2008-018162, English Translation.

*Primary Examiner* — Randy Gibson
*Assistant Examiner* — Gedeon M Kidanu
(74) *Attorney, Agent, or Firm* — Banner & Witcoff, Ltd.

(57) ABSTRACT

To detect humidity, used are a first series connection circuit connecting a thermistor and a fixed resistor via a node, a second series connection circuit connecting a resistance change type humidity sensor and the thermistor via the node, and a third series connection circuit connecting the humidity sensor and the fixed resistor via the node. A predetermined voltage is applied across the first circuit to detect a first voltage indicating temperature through the node, and secondly across the second circuit to detect a second voltage indicating a first humidity through the node, and finally across the third circuit to detect a third voltage indicating a second humidity through the node. Then, the first voltage is compared with a reference voltage and judgment is made, based on a comparison result, to determine which of the second voltage and the third voltage is relevant to use as a basis for outputting the humidity as detected.

14 Claims, 9 Drawing Sheets

(58) Field of Classification Search
CPC ............. G01N 33/0031; G01N 27/048; G01N 27/223; G01N 19/10; G01N 25/56; G01N 27/407
USPC ....... 73/335.02, 335.03, 335.05; 399/44, 94; 324/71.1, 693, 705, 712
See application file for complete search history.

(56) References Cited

U.S. PATENT DOCUMENTS

| | | | |
|---|---|---|---|
| 5,148,218 A | 9/1992 | Nakane et al. | |
| 5,170,210 A | 12/1992 | Saruwatari | |
| 5,623,330 A | 4/1997 | Ishibashi | |
| 5,656,928 A | 8/1997 | Suzuki et al. | |
| 6,281,963 B1 | 8/2001 | Takahata et al. | |
| 7,597,001 B2 | 10/2009 | Hayakawa | |
| 7,680,422 B2 | 3/2010 | Nakaue et al. | |
| 7,899,346 B2* | 3/2011 | Kubo | G03G 21/203 399/44 |
| 8,224,198 B2* | 7/2012 | Kubo | G01N 27/121 399/44 |
| 2007/0186650 A1 | 8/2007 | Hayakawa | |
| 2008/0056744 A1* | 3/2008 | Takahashi | G01J 1/04 399/49 |
| 2008/0112716 A1 | 5/2008 | Jeschonek | |
| 2009/0190942 A1* | 7/2009 | Kubo | G03G 21/203 399/44 |
| 2009/0297184 A1* | 12/2009 | Kubo | G03G 21/203 399/44 |
| 2011/0138908 A1* | 6/2011 | Liu | G01N 27/223 73/335.04 |
| 2014/0043601 A1* | 2/2014 | Takahashi | G01B 11/26 356/138 |

FOREIGN PATENT DOCUMENTS

| | | |
|---|---|---|
| JP | S61-128149 A | 6/1986 |
| JP | S64-088144 A | 4/1989 |
| JP | H03-138553 A | 6/1991 |
| JP | H05-149905 A | 6/1993 |
| JP | H06-221882 A | 8/1994 |
| JP | H07-311169 A | 11/1995 |
| JP | H08-029370 A | 2/1996 |
| JP | H09-005371 A | 1/1997 |
| JP | 2001-147139 A | 5/2001 |
| JP | 2001-153438 A | 6/2001 |
| JP | 2005-221484 A | 8/2005 |
| JP | 2006-275761 A | 10/2006 |
| JP | 2007-232428 A | 9/2007 |
| JP | 2007-248455 A | 9/2007 |
| JP | 2007-263702 A | 10/2007 |
| JP | 2009-180560 A | 8/2009 |
| JP | 2009-293942 A | 12/2009 |
| JP | 2013-096823 A | 5/2013 |

\* cited by examiner

FIG. 8

| | HUM DET MODE | 1ST HUM DET MODE | | 2ND HUM DET MODE | |
|---|---|---|---|---|---|
| P1 | Hiz | Hiz | H | L | H | L |
| P2 | H | L | L | H | Hiz | Hiz |
| P3 | L | H | Hiz | — | L | H |
| Pin | SAMPLING | — | SAMPLING | — | SAMPLING | — |

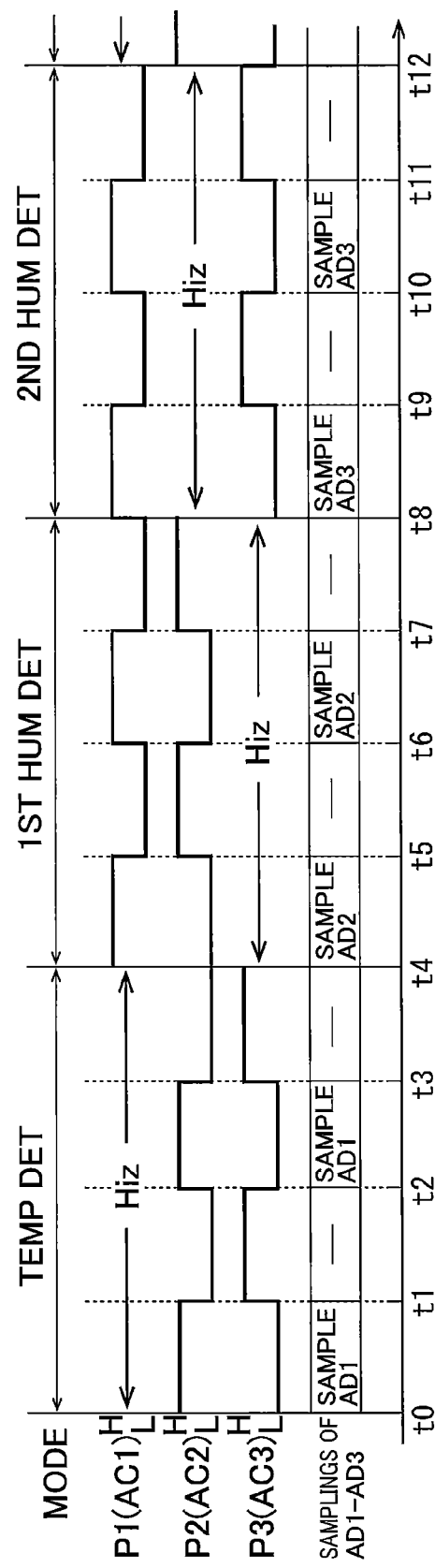

SENSOR DEVICE HAVING PLURAL RESISTANCE CHANGE SENSORS AND METHOD OF USING THE SAME

CROSS REFERENCE TO RELATED APPLICATION

This application claims priority from Japanese Patent Application No. 2013-062089 filed Mar. 25, 2013. The entire content of the priority applications is incorporated herein by reference.

BACKGROUND

1. Field of the Invention

The present invention relates generally to a sensor device and a method of using the same, and more particularly, to a sensor device having a plurality of resistance change type sensors (or variable resistance sensors) for sensing, for example, humidity and temperature.

2. Description of the Related Art

Japanese Patent Application Publication No. 2009-180560 discloses a sensor device having a detecting part and a controller, in which the outputs of the detecting part are applied to the controller. The detecting part includes a plurality of resistance change type sensors. Each resistance change type sensor outputs a voltage changeable depending upon the resistance of the sensor which in turn is changeable depending upon a parameter to be detected, such as humidity.

In this publication, the controller is provided with input terminals configured to separately and individually receive each output from each of the plurality of sensors. As such, the number of input terminals of the controller needs to be increased as the number of the sensors in the detecting part increases. However, it is inconvenient for the sensor device to replace or re-design the controller so as to be capable of accepting an increased number of outputs from the increased number of sensors.

SUMMARY

In view of the foregoing, it is an object of the invention to provide a sensor device having a plurality of resistance change type sensors, in which the number of lines for transmitting the sensor outputs does not need to be changed even if the number of sensors contained in the sensor device is increased.

In order to achieve the above and other objects, the invention provides according to one aspect, a sensor device that may include a first resistance change type sensor, a second resistance change type sensor, a fixed resistor, and a controller. The first resistance change type sensor has a first terminal and a second terminal and configured to detect a first parameter, such as temperature. The second resistance change type sensor has a third terminal and a fourth terminal connected to the first terminal and configured to detect a second parameter, such as humidity. The fixed resistor has a fifth terminal and a sixth terminal connected to both the first terminal and the fourth terminal. The controller has a first output port connected to the second terminal, a second output port connected to the third terminal, a third output port connected to the fifth terminal, and an input port connected to all of the first terminal, the fourth terminal and the sixth terminal. The controller may be configured to execute a first signal applying process, a first detection process, a second signal applying process, a second detection process, and a parameter detection process in the stated order.

In the first signal applying process, the first output port is rendered high impedance, and a predetermined voltage is applied across the second output port and the third output port. The predetermined voltage may be such a waveform that a first voltage level and a second voltage level are alternately changed.

In the first detection process, a first detection voltage applied to the input port is detected when the second output port is at the first voltage level and the third output port is at the second voltage level during execution of the first signal applying process.

In the second signal applying process, one of the second output port and the third output port is rendered high impedance. The predetermined voltage is applied across the first output port and remaining one of the second output port and the third output port.

In the second detection process, a second detection voltage applied to the input port is detected when the first output port is at the first voltage level and the second output port or third output port whichever is not rendered high impedance is at the second voltage level during execution of the second signal applying process.

In the parameter detection process, a value of the first parameter is determined using the first detection voltage and the second detection voltage.

According to another aspect of the invention, there is provided an image forming device that may include an image forming portion configured to form an image on an object based on image data, and the sensor device described above.

According to still another aspect of the invention, there is provided a method of detecting humidity. To implement the method, it is advisable to use a first series connection circuit connecting in series a thermistor and a fixed resistor via a node, a second series connection circuit connecting in series a resistance change type humidity sensor and the thermistor via the node, and a third series connection circuit connecting in series the resistance change type humidity sensor and the fixed resistor via the node.

The method may include a temperature detecting process, a first humidity detecting process, a second humidity detecting process, and a judgment process.

In the temperature detecting process, a predetermined voltage is applied across the first series connection circuit to detect a first voltage indicative of a temperature through the node. In the first humidity detecting process, the predetermined voltage is applied across the second series connection circuit to detect a second voltage indicative of a first humidity through the node. In the second humidity detecting process, the predetermined voltage is applied across the third series connection circuit to detect a third voltage indicative of a second humidity through the node. In the judgment process, the first voltage is compared with a reference voltage and judgment is made, based on a comparison result, to determine which of the second voltage and the third voltage is relevant to use as a basis for outputting the humidity.

BRIEF DESCRIPTION OF THE DRAWINGS

The particular features and advantages of the invention as well as other objects will become apparent from the following description taken in connection with the accompanying drawings, in which:

FIG. 8 is a table showing a printer port status in each of various detection modes to be selectively executed in the humidity detection process.

FIG. 9 a timing chart for explaining the humidity detection process.

DETAILED DESCRIPTION

One embodiment of the invention will be described with reference to the accompanying drawings.

<Printer's Overall Structure>

Figure 1:
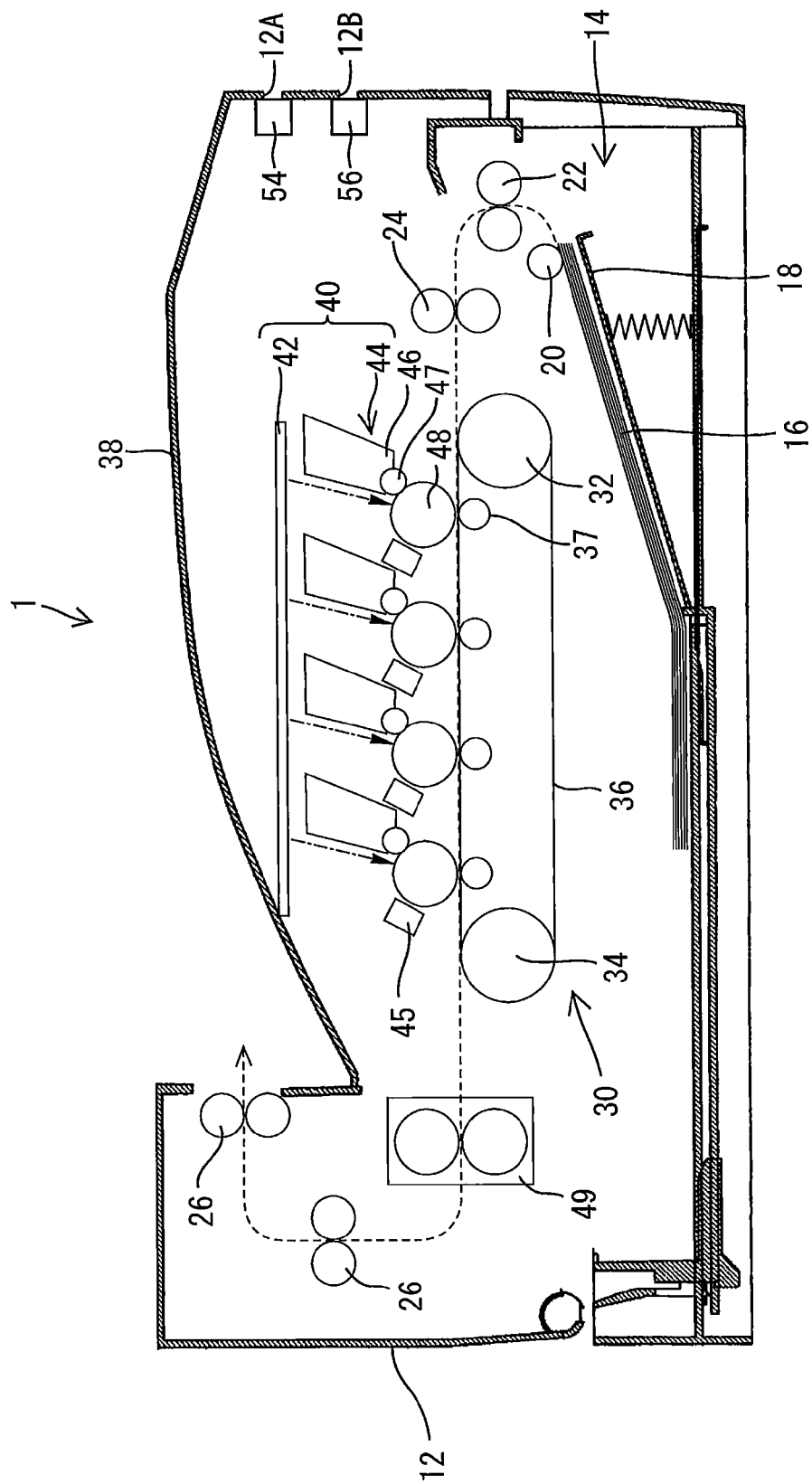
FIG. 1 is a schematic vertical cross-sectional view showing a color laser printer according to one embodiment of the invention.

FIG. 1 is a vertical cross-sectional view of a printer 1, which is one of image forming devices, according to one embodiment of the invention. As shown in FIG. 1, the printer 1 is a direct-transfer, tandem type color laser printer capable of forming a full-color image using four kinds of color toner of yellow, magenta, cyan and black.

A print medium storage tray 14 is accommodated in a casing 12 of the printer 1 and disposed in the lower portion thereof. A plenty of sheet-type print media 16, such as sheets of paper, is stacked in the tray 14. The tray 14 is capable of being drawn out of the casing 12 for the user to supplement the print media 16. Upon completion of supplementing the print media 16, the tray 14 is returned to the right position within the casing 12. The print media stacked in the tray 14 is urged against a pickup roller 28 by a pressing plate 18 upwardly biased by a spring. In accordance with rotations of the pickup roller 28, the uppermost print medium 16 is fed toward a nip between a pair of conveying rollers 22 and further away toward a nip between a pair of registration rollers 24. The registration rollers 24 hold the print medium 16 until it is time for it to be released, and correct the orientation of an obliquely conveyed print medium 16. The print medium 16 having released from the registration rollers 24 is conveyed further toward a conveying section 30.

The conveying section 30 includes a pair of support rollers 32, 34, an endless belt 36, and a plurality of transfer rollers 37 (four in this embodiment). The endless belt 36 is wound around the spaced-apart two support rollers 32, 34 with taut. The transfer rollers 37 are juxtaposed along the print medium conveying direction at equi-pitch inside the endless belt 36. The support rollers 32, 34 are coupled to a motor (not shown) and thereby rotated counter-clockwise, so that the upper part of the endless belt 36 is moved leftward and the lower part thereof rightward.

An image forming unit 40 is disposed above the upper part of the endless belt 36, and includes a scanning section 42 and a process section 44. The process section 44 includes four sets of process units corresponding to four kinds of color toner. Each process unit includes a photosensitive drum 48, a developing cartridge 46, and a charger 45. The charger 45 uniformly charges the peripheral surface of the photosensitive drum 48 to positive polarity. Color toner is contained in the developing cartridge 46 and a developing roller 47 is rotatably disposed in the developing cartridge 46. A developing bias voltage is applied to the developing roller 47 by a high voltage power supply 80 (see FIG. 2). The developing roller 47 applied with the developing bias voltage supplies toner contained in the developing cartridge 46 to the photosensitive drum 48.

The scanning section 42 is disposed above the process section 44. The scanning section 42 is configured to irradiate a laser beam L onto the photosensitive drum 49 based on color-based image data fed from a RAM 46 under the aegis of a central processing unit 62 (see FIG. 2) which will hereinafter be referred to as "CPU 62". As a result of laser beam irradiation, an electrostatic latent image is formed on the surface of the photosensitive drum 48. The electrostatic latent image thus formed corresponds to an image to be formed on the print medium 16. The latent image is developed by the toner supplied by the developing roller 47, and a visible toner image is formed thereon.

As the photosensitive drum 48 rotates, the toner image formed thereon reaches and passes a transfer position between the photosensitive drum 48 and the endless belt 36. The toner image is transferred on the print medium 16 when a transfer bias voltage is applied to the transfer roller 37. The transfer roller 37 is rotatably disposed in confrontation with the photosensitive drum 48 with the upper part of the endless belt 36 interposed therebetween. As the print medium 16 on the endless belt 36 moves, four color toner images are sequentially transferred on the print medium 16 so as to be superposed one on the other. In this manner, a full-color toner image is formed on the print medium 16 and is then thermally fixed by a thermal fixing device 49. The print medium 16 on which the color image is formed is conveyed and discharged by a pair of conveying rollers 26 out to the casing 12 and placed on a discharge tray 38 formed on the upper surface of the casing 12. In the printer 1 shown in FIG. 1, the image forming unit 40 corresponds to an image forming portion configured to form an image on an object based on image data provided in an image forming device.

Slits 12A and 12B are formed at upper positions of the rear wall of the casing 12 so as to be in fluid communication with external environment. The positions where the slits 12A and 12B are formed are not limited to the above-described positions but may be formed in other appropriate positions. A humidity sensor 54 and a temperature sensor 56 are disposed inside the casing 12 and in positions where the slits 12A and 12B are formed. The humidity sensor 54 is provided for sensing ambient humidity through the slit 12A and the temperature sensor 56 for sensing ambient temperature through the slit 12B. These two slits 12A and 12B are formed in adjacent positions so that the ambient air subject to sensing is substantially the same. In this embodiment, a thermistor is used as the temperature sensor. As is known in the art, the thermistor has a temperature-dependent resistance. Also, a resistor having a humidity-dependent resistance is used as the humidity sensor. The temperature sensor 56 using the thermistor is one example of a first temperature-dependent resistance change type sensor and the humidity sensor 54 is one example of a second humidity-dependent resistance change type sensor. The CPU 62 sets the transfer bias voltage to be applied to the transfer rollers 37 based on the ambient humidity and ambient temperature detected by the humidity sensor 54 and the temperature sensor 56.

<Electrical Arrangement of Sensor Device Provided in Printer>

Figure 2:
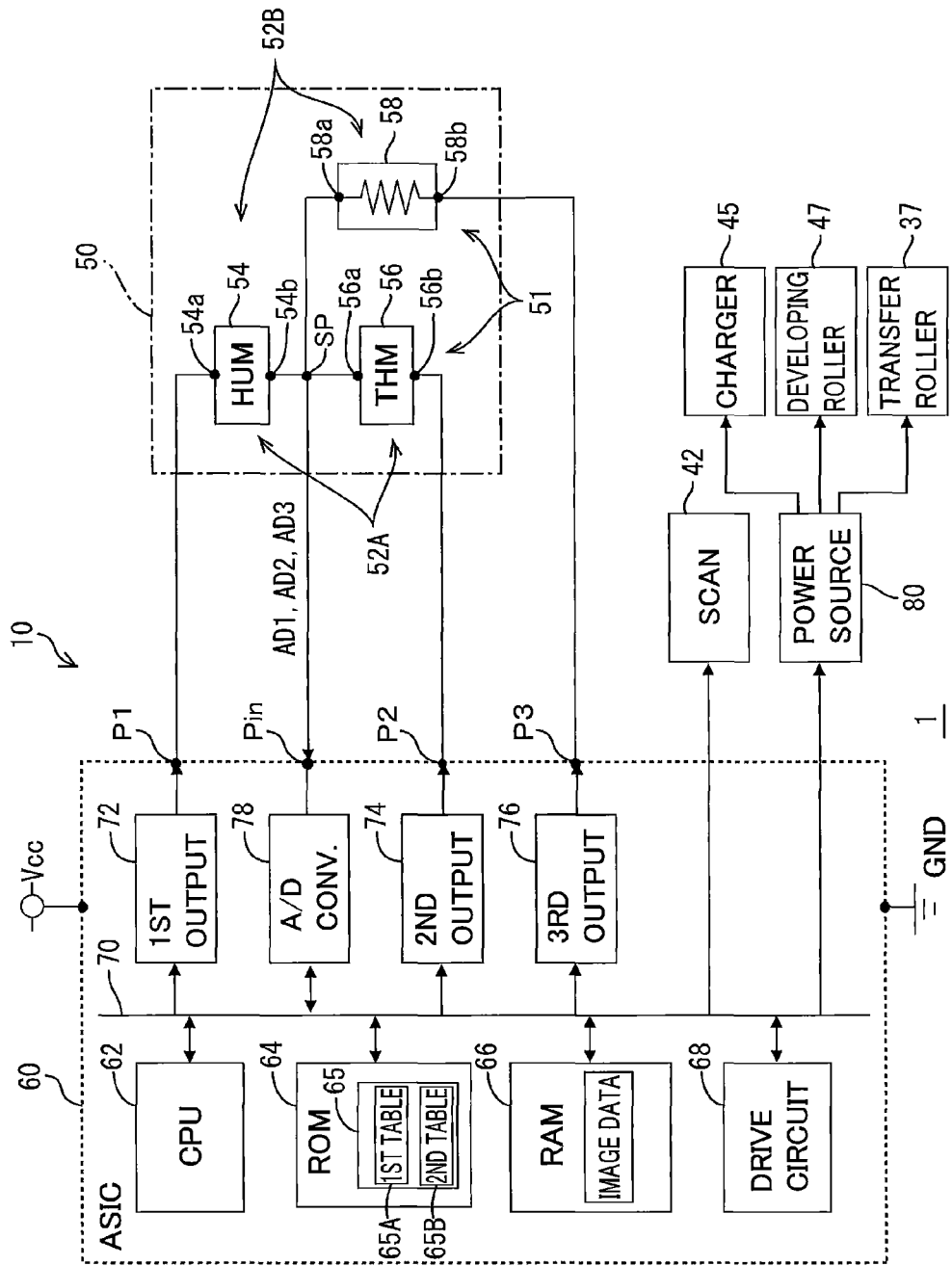
FIG. 2 is a block diagram showing an electrical arrangement of the printer shown in FIG. 1.

FIG. 2 shows, in a block form, an electrical arrangement of a sensor device 10 provided in the printer 1 and the parts of the printer 1 subject to control based on the outputs from the sensor device 10. The sensor device 10 includes an application specific integrated circuit 60 (hereinafter referred to as "ASIC 60") for controlling the scanning section 42 and the high voltage power source 80 which in turn controls the chargers 45, developing rollers 47 and transfer rollers 37.

The ASIC 60 is applied with drive voltage Vcc from an external power source and connected to ground. The ASIC 60 includes the CPU 62, ROM 64, RAM 66, drive circuit 68, first output circuit 72, second output circuit 74, third output circuit 76, analog-to-digital converter 78, first to third output ports P1, P2, P3, and input port Pin, all of which are connected to a bus 70. Also, the scanning section 42 and the high voltage power source 80 are connected to the bus 70. The ASIC 60 illustrated in FIG. 2 is one example of a controller contained in the printer 1.

The ROM 64 stores various programs and a table 65 used for controlling the operation of the printer 1. The CPU 62 controls the various parts of the printer 1 in accordance with the programs retrieved from the ROM 64. The table 65 includes a first humidity sensing table 65A and a second humidity sensing table 65B. The CPU 62 refers to the table 65 when detecting the ambient humidity.

The drive circuit 68 is connected to a motor (not shown) and transmits pulse signals thereto in response to instructions fed from the CPU 62. The motor rotates in accordance with the pulse signals fed from the drive circuit 68. Rotations of the motor rotate medium conveying rollers, and rotations of the rollers convey the print medium 16 along the conveying path.

The ASIC 60 includes a first signal output circuit 72, a second signal output circuit 74 and a third signal output circuit 76. The first to third signal output circuits 72, 74, 76 apply first to third output signals AC1, AC2, AC3 to the first to third output ports P1, P2, P3 respectively, in response to the instructions from the CPU 62. As shown in FIG. 9, each of the first to third output signals AC1, AC2, AC3 is a rectangular waveform signal changing between a high (H) level voltage equal to the power source voltage Vcc and a low (L) level voltage equal to the ground voltage (GND) every half cycle (180 degrees). In this embodiment, the power source voltage Vcc, i.e., H level, is 3.3 volts, and the ground voltage (GND), i.e., L level, is 0 (zero) volt.

The first output signal AC1 and the second output signal AC2 are reversed phase signals such that the two signals are the same waveform signals but the phase of one signal is delayed or advanced by 180 degrees with respect to the other signal. More specifically, the rising edge of the first output signal AC1 is in coincidence with the falling edge of the second output signal AC2, and the falling edge of the first output signal AC1 is in coincidence with the rising edge of the second output signal. The H level duration of the first output signal AC1 is equal to the L level duration of the second output signal, and inversely the L level duration of the first output signal AC1 is equal to the H level duration of the second output signal AC2. The same is true with respect to the relation between the second output signal AC2 and the third output signal AC3 and between the third output signal and the first output signal AC1.

The humidity sensor 54 and the temperature sensor 56 are connected in series between the first output port P1 and the second output port P2 as shown in FIG. 2. In such a configuration, when the first output signal AC1 is at the H level and the second output signal AC2 is at the L level, the voltage at the first terminal 54*a* of the humidity sensor 54 is higher than the voltage at the second terminal 54*b* of the humidity sensor 54. In this condition, a positive polarity divided voltage is developed between the first terminal 54*a* and the second terminal 54*b* of the humidity sensor 54. Inversely, when the first output signal AC1 is at the L level and the second output signal AC2 is at the H level, the voltage at the first terminal 54*a* of the humidity sensor 54 is lower than the voltage at the second terminal 54*b* of the humidity sensor 54. In this condition, a negative polarity divided voltage is developed between the first terminal 54*a* and the second terminal 54*b* of the humidity sensor 54. As such, the positive and negative polarity voltages with the same voltage in absolute value are alternately applied to the humidity sensor 54. In other words, the humidity sensor 54 senses the ambient humidity while being applied with the AC voltage. Each of the output signals AC1, AC2, AC3 is not limited to the above-described rectangular waveform but may be other form, such as trapezoidal waveform.

The AC type voltage application to the humidity sensor 54 is more advantageous than a DC type voltage application thereto. The humidity sensor of the type in which the resistance of the humidity sensor changes depending upon humidity typically includes a humidity sensitive material, such as an electrically conductive high molecular membrane in which ions are allowed to be movable therein. The DC type voltage application to such a sensor yields electrical polarization in the high molecular membrane, which hinders accurate measurements of the resistance of the sensor.

As shown in FIG. 2, the sensing part 50 includes the humidity sensor (HUM) 54, the thermistor (THM) 56 serving as the temperature sensor, and a fixed resistor 58. The humidity sensor 54 and the thermistor 56 are connected in series across the first output port P1 and the second input port P2. Specifically, the humidity sensor 54 has a first terminal 54*a* connected to the first output port P1 and a second terminal connected to the first terminal 56*a* of the thermistor 56 via a node SP. The thermistor 56 has a second terminal 56*b* connected to the second output port P2.

The thermistor 56 and the fixed resistor 58 are connected in series across the second output port P2 and the third output port P3. Specifically, the second terminal 56*b* of the thermistor 56 is connected to the second output port P2, the first terminal 56*a* of the thermistor 56 is connected to the first terminal 58*a* of the fixed resistor 58 via the node SP, and the second terminal 58*b* of the fixed resistor 58 is connected to the third output port P3.

The first output port P1 of the ASIC 60 is connected to the first terminal 54*a* of the humidity sensor 54, the second output port P2 of the ASIC 60 is connected to the second terminal 56*b* of the thermistor 56, and the third output port P3 is connected to the second terminal 58*b* of the fixed resistor 58. Further, the input port Pin of the ASIC 60 is connected to the node SP connecting the humidity sensor 54, thermistor 56 and fixed resistor 58.

With the above-described configuration, the sensing part 50 includes a temperature sensing circuit 51 in which the thermistor 56 and the fixed resistor 58 are connected in series across the second and third output ports P2 and P3, a first humidity sensing circuit 52A in which the humidity sensor 54 and the thermistor 56 are connected in series across the output ports P1 and P2, and a second humidity sensing circuit 52B in which the humidity sensor 54 and the fixed resistor 59 are connected in series across the output ports P1 and P3.

In each of the above-described three sensing circuits, the divided voltage developed across the humidity sensor 54 or the thermistor 56 or across the fixed resistor 58 appears at the node SP and is applied to the input port Pin of the ASIC 60. The voltage supplied from the temperature sensing circuit 51 is applied to the input port Pin as a detection voltage AD1, the voltage supplied from the first humidity sensing circuit 52A as a detection voltage AD2, and the voltage supplied from the second humidity sensing circuit 52B as a detection voltage AD3. The analog-to-digital converter 78 of the ASIC 60 separately receives the detection voltages AD1, AD2 and AD3 at a sampling timing specified by the CPU 62 (see FIG. 9). The analog-to-digital converter 78 converts the detection voltages in the form of an analog signal to a digital signal.

Figure 3:
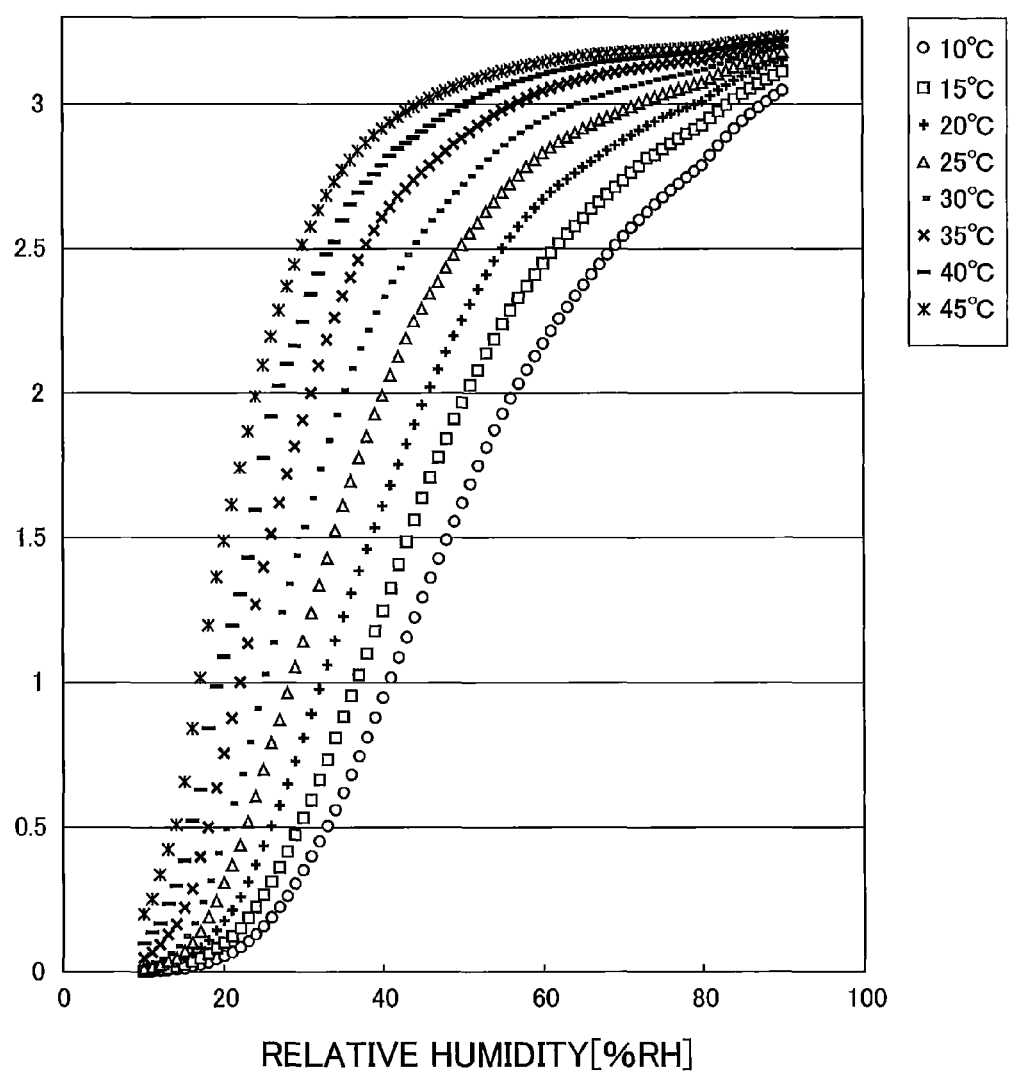
FIG. 3 is a graphical representation showing a relationship between humidity values and detection voltages from a first circuit configured from a humidity sensor and a thermistor connected in series under varying environmental temperatures.
Figure 4:
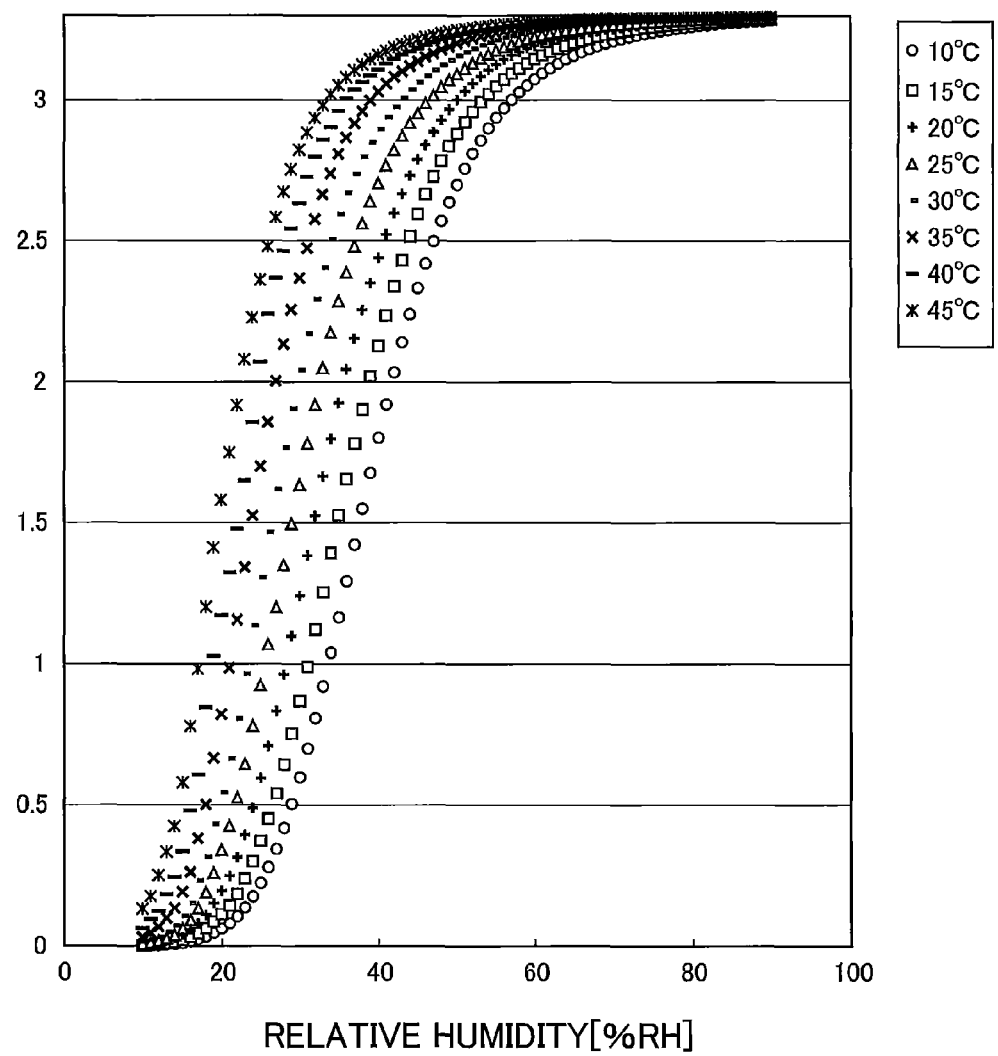
FIG. 4 is a graphical representation showing a relationship between humidity values and detection voltages from a second circuit configured from a humidity sensor and a fixed resistor connected in series under varying environmental temperatures.

The humidity sensor 54 has a temperature-dependent humidity-versus-resistance characteristic (see FIGS. 3 and 4). For example, the humidity sensor 54 has such a characteristic that it's resistance changes from 10 Mega-Ohm to 1 Ohm with respect to the change in relative humidity in a range from 10 to 80% RH and the change in temperature in a range from 5 to 45 degrees Celsius. Hereinafter, the "relative humidity" will simply be referred to as "humidity" and its unit will be expressed with "%". The resistance of the humidity sensor 54 is, for example, about 50 Ohm with the humidity of 50% and the temperature of 25 degrees Celsius. The humidity sensor 54 used in this embodiment exhibits a negative resistance property with respect to both humidity and temperature. Specifically, the humidity sensor 54 exhibits such a characteristic that an increase in humidity results in a decreased resistance, and an increase in temperature results in a decreased resistance. As such, the resistance of the humidity sensor 54 is relatively high under low-temperature/low-humidity whereas the resistance of the humidity sensor 54 is relative low under high-temperature/high-humidity.

The thermistor 56 has a negative temperature coefficient (NTC), so that the resistance of the thermistor 56 decreases as the temperature increases and the resistance of the thermistor 56 increases as the temperature decreases. For example, the resistance of the thermistor 56 decreases from 3500 Kilo-Ohm to 44 Kilo-Ohm attendant to the temperature increase from minus 10 to 80 degrees Celsius. In this embodiment, the fixed resistor 58 has a resistance of 680 kilo-Ohm which is roughly equal to the resistance of the thermistor 65 (470 Kilo-Ohm) at 25 degrees Celsius. The fixed resistor 58 needs to be selected to have a relevant resistance falling within a selected range to optimize the temperature detection accuracy. The above-noted resistances of the thermistor 56 and the fixed resistor 58 are one example to gain high humidity detection accuracy under low-temperature/low-humidity circumstance. In performing the humidity detection, selection of the thermistor 56 and the fixed resistor 58 need to be made depending upon the temperature and humidity detection circumstance in order to optimize the humidity detection accuracy.

<Humidity Detection>

Next, a humidity sensing will be described while referring to FIGS. 3 to 9.

Referring to FIGS. 3 to 6, first and second humidity detection characteristic curves will be described. The first humidity detection characteristic curve is obtained by the first humidity sensing circuit 52A in which the humidity sensor 54 and the thermistor 56 are connected in series across the first and second output ports P1 and P2 of the ASIC 60. The second humidity detecting characteristic curve is obtained by the second humidity sensing circuit 52B in which the humidity sensor 54 and the fixed resistor 58 are connected in series across the first and third output ports P1 and P3 of the ASIC 60. In this embodiment, either one of the first and second humidity sensing circuits 52A and 52B is selectively used for the reasons stated below.

The humidity sensor 54 exhibits a resistance characteristic such that the resistance is fairly large under the low-temperature/low-humidity circumstance. In order to increase the detection accuracy, it is required that the counterpart resistor of the serially connected humidity sensing circuit have a large resistance to output a high level divided voltage across the counterpart resistor. On the other hand, the resistance characteristic of the humidity sensor exhibits that the resistance is small under the high-temperature/high-humidity circumstance. In order to increase the detection accuracy under such a circumstance, it is required that the counterpart resistor of the serially connected humidity sensing circuit have a small resistance to output a high level divided voltage. As such, the use of the same counterpart resistor makes it difficult to attain high detection accuracy in both the low-temperature/low-humidity circumstance and the high-temperature/high-humidity circumstance. To solve such a difficulty, the thermistor 56 and the fixed resistor 58 are selectively used as the counterpart resistor of the serially connected humidity sensing circuit, whereby detection of the humidity can be achieved with excellent accuracy regardless of the degrees of temperature and humidity.

FIG. 3 shows a first humidity sensing characteristic to be detected by the use of the first serially connected humidity sensing circuit 52A. This characteristic shows that the detection voltage AD2 developed across the thermistor 56 does not saturate in a range except for the low-temperature/low-humidity range, so that detection of humidity can be achieved with fairly good accuracy. Particularly, in the high-temperature/high-humidity range, the use of the first humidity sensing characteristic is more advantageous in terms of detection accuracy than a second humidity sensing characteristic shown in FIG. 4 which shows the characteristic to be detected by the use of the second serially connected humidity sensing circuit 52B.

Figure 5:
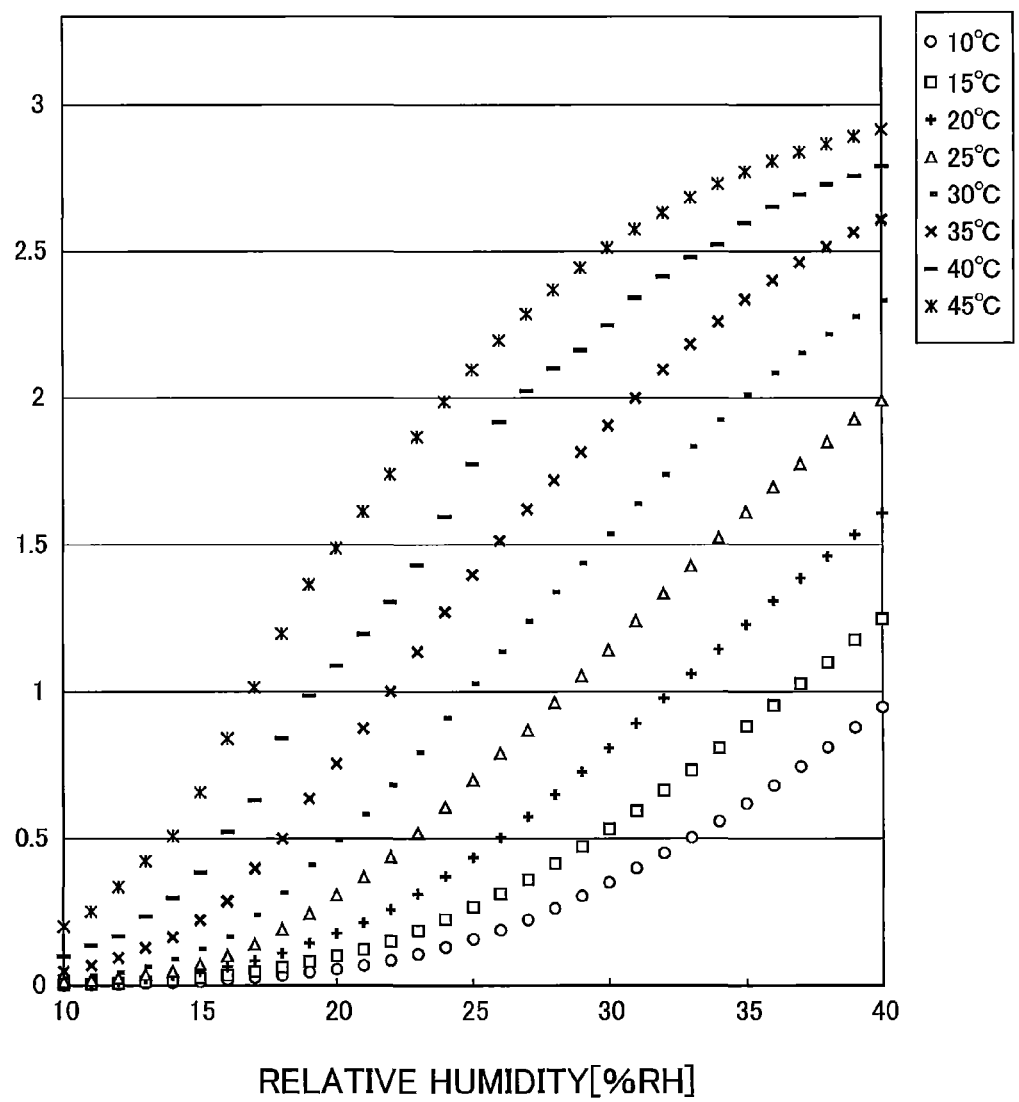
FIG. 5 is an enlarged graphical representation showing a low humidity region in the graph of FIG. 3.
Figure 6:
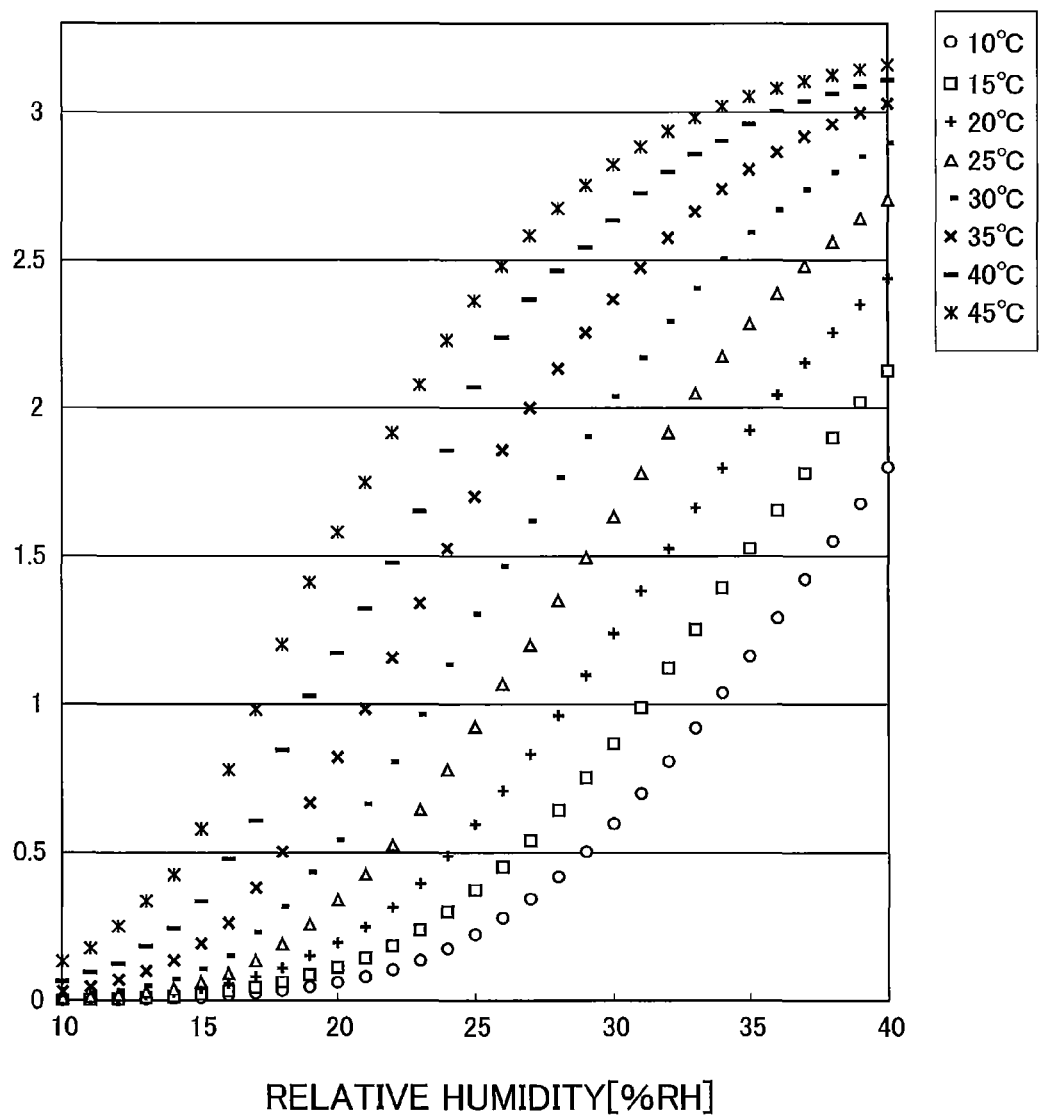
FIG. 6 is an enlarged graphical representation showing a low humidity region in the graph of FIG. 4.

On the other hand, in the low-temperature/low-humidity range, the second humidity sensing characteristic is more advantageous than the first humidity sensing characteristic in terms of detection accuracy as can be seen from FIGS. 5 and 6. Because, in the low-temperature/low-humidity range, the detection voltage AD3 developed across the fixed resistor 58 changes at a rate higher than the detection voltage AD2 developed across the thermistor 56. For the reasons stated above, in accordance with the embodiment, depending upon the detection range of the humidity, the first humidity detection voltage AD2 obtained from the first serially connected humidity sensing circuit 52A and the second humidity detection voltage AD3 obtained from the second serially connected humidity sensing circuit 52B are selectively used to attain high detection accuracy in both the low-temperature/low-humidity range and the high-temperature/high-humidity range.

Data representing the humidity-versus-detection voltage characteristic for each temperature is written in a first humidity detection table 65A stored in the ROM 64. More specifically, the first humidity detection data AD2 and the corresponding humidity are stored in the ROM 64 in association with the temperature detection voltage AD1. Similarly, data representing the humidity-versus-detection voltage characteristic for each temperature is written in a second humidity detection table 65B stored in the ROM 64. Specifically, the second humidity detection data AD3 and the corresponding humidity are stored in the ROM 64 in association with the temperature detection voltage AD1. Further, data representing the characteristic of the resistance of the thermistor 56 and temperature may also be stored in the ROM 64. It should be noted that the detection voltage AD1 corresponds to or equivalent to the resistance of the thermistor 56.

The CPU 62 detects the humidity based on the temperature detection voltage AD1 detected by the temperature detecting serially connected circuit 51, the first humidity detecting voltage AD2, and data written in the first humidity detection table 65A. Specifically, the humidity can be obtained by designating the temperature detecting voltage AD1 and the first humidity detecting voltage AD2 on the first humidity detecting table 65A. Alternatively, the CPU 62 detects the humidity while referring to the temperature detecting voltage AD1, the second humidity detecting voltage AD3, and the second humidity detecting table 65B. Specifically, the humidity can be obtained by designating the temperature detecting voltage AD1 and the second humidity detecting voltage AD3 on the second humidity detecting table 65B.

The humidity detection voltages AD2 and AD3 on the axis of ordinate in the graphs shown in FIGS. 3 to 6 correspond to the resistance of the humidity sensor 54. Accordingly, the axis of ordinate in the graphs can be understood as indicating the resistance of the humidity sensor 54. In this embodiment, however, the humidity detecting voltages AD2 and AD3 are the voltages appearing at the node SP. More specifically, the voltage AD2 is the divided voltage developed across the thermistor 56 in the serially connected circuit of the humidity sensor 54 and the thermistor 56, and the voltage AD3 is the divided voltage developed across the fixed resistor 58 in the serially connected circuit of the humidity sensor 54 and the fixed resistor 58 when the first output port P1 is at a H-level voltage. With such a circuit configuration, the graphs shown in FIGS. 3 to 6 indicate that as the humidity detecting voltages AD2 and AD3 become greater, the resistance of the humidity sensor 54 becomes smaller.

Next, the humidity detecting process will be described while referring to FIGS. 7 to 9. The humidity detecting process is executed by the CPU 62 in accordance with the program stored in the ROM 64. The program runs in response to a print instruction entered by a user, for example. The humidity detecting process may not necessarily be implemented by the user's print instruction but be implemented at every predetermined interval during printing operation.

Figure 7:
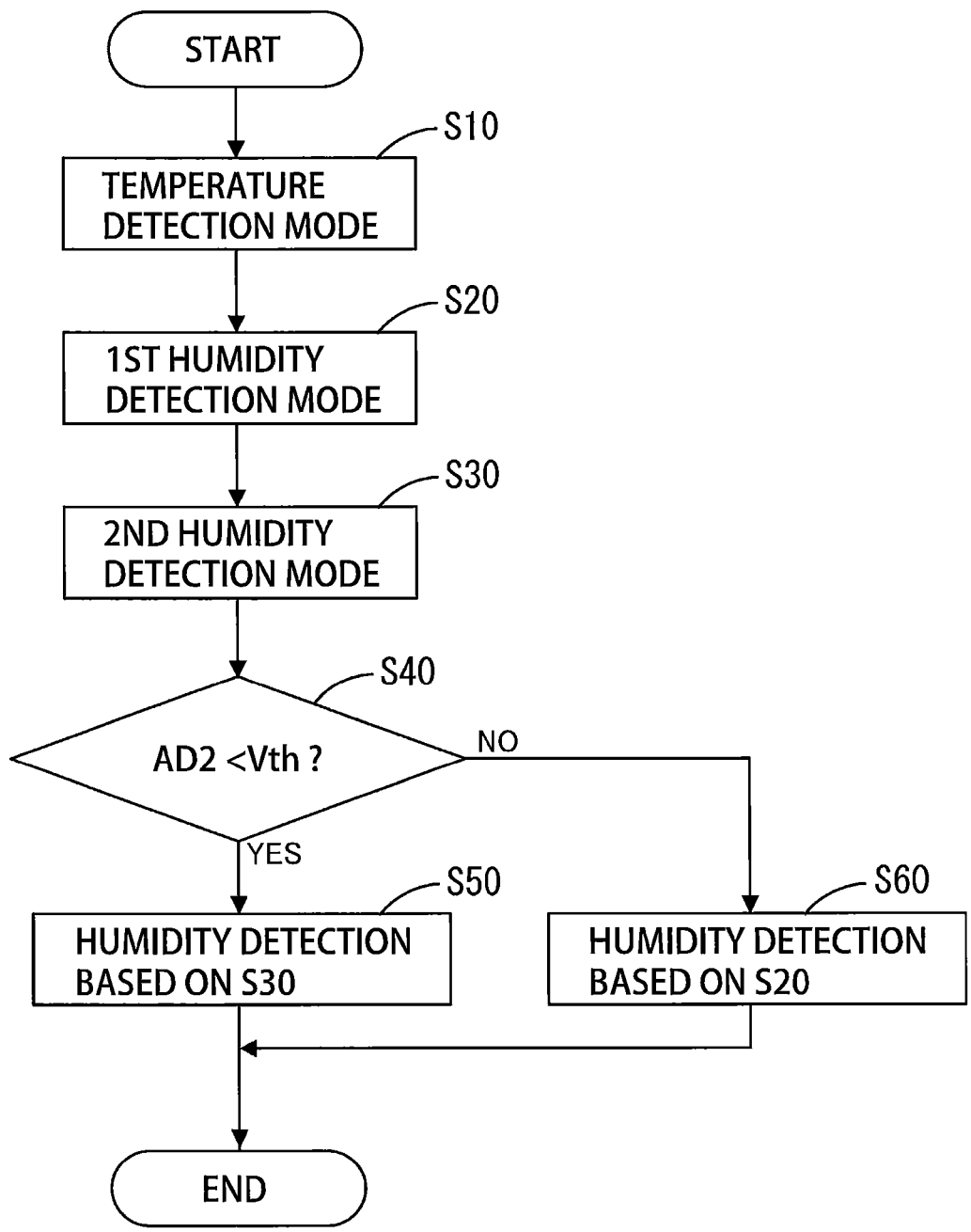
FIG. 7 is a flowchart illustrating a humidity detection process.

As shown in FIG. 7, the CPU 62 first executes a temperature detection mode (S10). In the temperature detecting mode, as shown in FIGS. 8 and 9, the second output signal AC2 output from the second output port P2 has an H-level duration and an L-level duration which are alternately repeated. The third output signal AC3 output from the third output port P3 has also an H-level duration and an L-level duration which are alternately repeated. The second and third output signals AC2 and AC3 are in phase with each other but the level of one signal is in reversed relation with that of the remainder. Specifically, when the signal AC2 is at the H-level, the signal AC3 is at the L-level, and vice versa. Under the temperature detection mode, the first output port P1 is held in a high impedance state (Hiz). As shown in FIG. 9, the temperature detecting mode is effected in the duration from t0 to t4 as shown in FIG. 9.

In the sampling period at which the second output port P2 (the second output signal AC2) is at the H-level and the third output port P3 (third output signal AC3) is at the L-level, the analog-to-digital converter 78 inputs the temperature detecting voltage AD1 appearing at the node SP and converts the inputted voltage AD1 to a digital value in accordance with the instructions from the CPU 62. The CPU 62 instructs the RAM 66 to temporarily store the digital value AD1. In this embodiment, the temperature detection is carried out twice in succession and the two digital values are averaged. The averaged digital value is used as a temperature digital value AD1. The sampling periods to obtain two temperature detection voltages are the time duration from t0 to t1 and the time duration from t2 to t3 in FIG. 9.

As shown in FIG. 7, the CPU 62 next executes a first humidity detection mode (S20). In the first humidity detecting mode, as shown in FIGS. 8 and 9, the first output signal AC1 output from the first output port P1 has an H-level duration and an L-level duration which are alternately repeated. The second output signal AC2 output from the second output port P2 has also an H-level duration and an L-level duration which are alternately repeated. The first and second output signals AC1 and AC2 are in phase with each other but the level of one signal is in reversed relation with that of the remainder. Specifically, when the signal AC1 is at the H-level, the signal AC2 is at the L-level, and vice versa. Under the first humidity detection mode, the third output port P3 is held in Hiz state. As shown in FIG. 9, the first humidity detecting mode is effected in the duration from t4 to t8 as shown in FIG. 9.

In the sampling period at which the firsts port P1 (the first output signal AC1) is at the H-level and the second port P2 (second output signal AC2) is at the L-level, the analog-to-digital converter 78 inputs the first humidity detecting voltage AD2 appearing at the node SP and converts the inputted voltage AD2 to a digital value in accordance with the instructions from the CPU 62. The CPU 62 instructs the RAM 66 to temporarily store the digital value AD2. In this embodiment, the first humidity detection is carried out twice in succession and the two digital values are averaged. The averaged digital value is used as a first humidity digital value AD2. The sampling periods to obtain two first humidity detection voltages are time duration from t4 to t5 and time duration from t6 to t7 in FIG. 9.

Next, the CPU 62 executes a second humidity detection mode (S30). In the second humidity detecting mode, as shown in FIGS. 8 and 9, the first output signal AC1 output from the first output port P1 has an H-level duration and an L-level duration which are alternately repeated. The third output signal AC3 output from the third output port P3 has also an H-level duration and an L-level duration which are alternately repeated. The first and third output signals AC1 and AC3 are in phase with each other but the level of one signal is in reversed relation with that of the remainder. Specifically, when the signal AC1 is at the H-level, the signal AC3 is at the L-level, and vice versa. Under the second humidity detection mode, the second output port P2 is held in Hiz state. As shown in FIG. 9, the second humidity detecting mode is effected in the duration from t8 to t12 as shown in FIG. 9.

In the sampling period at which the firsts port P1 (the first output signal AC1) is at the H-level and the third port P3 (third output signal AC3) is at the L-level, the analog-to-digital converter 78 inputs the second humidity detecting voltage AD3 appearing at the node SP and converts the inputted voltage AD3 to a digital value in accordance with the instructions from the CPU 62. The CPU 62 instructs the RAM 66 to temporarily store the digital value AD3. In this embodiment, the second humidity detection is carried out twice in succession and the two digital values are averaged. The averaged digital value is used as a second humidity digital value AD3. The sampling period to obtain two second humidity detection voltages is time duration from t8 to t12. in FIG. 9.

In the sampling period at which the first port P1 (the first output signal AC1) is at the H-level and the third port P3 (third output signal AC3) is at the L-level, the analog-to-digital converter 78 inputs the second humidity detecting voltage AD3 appearing at the node SP and converts the inputted voltage AD3 to a digital value in accordance with the instructions from the CPU 62. The CPU 62 instructs the RAM 66 to temporarily store the digital value AD3. In this embodiment, the second humidity detection is carried out twice in succession and the two digital values are averaged. The averaged digital value is used as a second humidity digital value AD3. The sampling periods to obtain two second humidity detection voltages are time duration from t8 to t9 and time duration from t10 to t11 in FIG. 9.

Then, the CPU 62 determines whether the first humidity detecting voltage AD2 detected under the first humidity detecting mode is smaller than a threshold voltage Vth (S40). As shown in FIGS. 3 and 4, both the first and second humidity detecting characteristics can provide good detection accuracy in the mid-range of humidity and temperature, or normal humidity and normal temperature. Therefore, the threshold voltage Vth is selected from a voltage range corresponding to the normal temperature and normal humidity. For example, the threshold voltage Vth is set to 1.5 volts.

When determination is made so that the first humidity detecting voltage AD2 is smaller than the threshold voltage Vth, e.g., 1.5 volts, (S40:YES), the CPU 62 detects the humidity based on the digital value AD1 representing the detected temperature, the digital value AD3 obtained under the second humidity detecting mode, and the second humidity detection table 65B (S50). The second humidity detection table 65B includes digital values AD1, digital values AD3, and humidity values correlated to one another. Specifically, with the second humidity detection table 65B, a humidity value can be specified by designating one of the digital value AD1 and one of the digital values AD3 given with respect to the designated digital value AD1. The second humidity detection table 65B outputs data representing the humidity value upon receipt of data regarding the digital values AD1 and AD3. The CPU 62 can thus detect and recognize the humidity. Based on the detected humidity, the CPU 62 sets transfer bias applied to the transfer section.

On the other hand, when determination is made so that the first humidity detecting voltage AD2 is not smaller than the threshold voltage Vth, that is, when the humidity detecting voltage AD2 is equal to or larger than the threshold voltage Vth (S40: NO), the CPU 62 detects the humidity based on the digital value AD1 representing the detected temperature, the digital value AD2 obtained under the first humidity detecting mode, and the first humidity detection table 65A (S60). The first humidity detection table 65A includes digital values AD1, digital values AD2, and humidity values correlated to one another. Specifically, with the first humidity detection table 65A, a humidity value can be specified by designating one of the digital value AD1 and one of the digital values AD2 given with respect to the designated digital value AD1. The first humidity detection table 65A outputs data representing the humidity value upon receipt of data regarding the digital values AD1 and AD2. The CPU 62 can thus detect and recognize the humidity.

As described, the CPU 62 refers to the first humidity detection table 65A and obtains a humidity value using the temperature detecting voltage AD1 and the first humidity detecting voltage AD2. A humidity value under the current temperature can be detected with a simplified humidity detection process in which all the jobs need for the CPU 62 to implement are to detect the temperature detecting voltage AD1 and the first humidity detecting voltage AD2 and to refer to the first humidity detection table 65A.

In the embodiment described above, the voltage appearing at the node SP is sampled twice in each mode and the averaged value is used as the detected value. However, this is only an example and the invention is not limited thereto. For example, sampling the voltage appearing at the node SP may be sampled once the sampled voltage may be used as the detected voltage. Or, the voltage appearing at the node SP may be sampled twice or more and an average value may be used as the detected voltage.

In the above-described embodiment, the sampling period is set to durations of t0 to t1, t4 to t5, t8 to t9 in the time chart of FIG. 9. That is, sampling the voltages at the node SP is performed when the second port is in H-level and the third port, L-level, when the first port is in H-level and the second port, L-level, and when the first port is in H-level, and the third port, L-level. However, when sampling is to be performed is not limited to those described above. For example, sampling may be performed when the second port is in L-level and the third port, H-level, when the first port is in L-level and the second port, H-level, and when the first port is in L-level, and the third port, H-level (see FIG. 8). If the sampling is performed at such timings, the sampled voltages are not the same as those in the above-described embodiment. Accordingly, the tables 65A and 65B need to be modified.

According to the sensor device described above, the voltage AD1 indicative of the temperature, and the voltages AD2 and AD3 indicative of the humidity under different temperature ranges are detected in time-division manner through a common input terminal Pin. Thus, the number of input terminals does not need to be increased unlike the conventional sensor device.

Further, the humidity sensor 54 according to the above-described embodiment uses the temperature-dependent resistance versus humidity characteristics as shown in FIGS. 3 and 4 to obtain the voltage AD1 using the thermistor 54, the voltage AD2 indicative of the first humidity detected under the first humidity detecting mode, and the voltage AD3 indicative of the second humidity detected under the first humidity detecting mode. Thus, the humidity sensor 54 described above can correct the influence of temperature imposed thereupon in providing the detection results. This means that the detection accuracy is improved.

In the above-described embodiment, the first humidity detecting mode is implemented in such a manner that the third port P3 is held in high impedance state and the output voltages AC are applied to the first and second ports P2 and P3 to detect the voltage AD2 applied to the input port Pin. The second humidity detecting mode is implemented in such a manner that the second port P2 is held in high impedance state and the output voltages AC are applied to the first and third ports P1 and P3 to detect the voltage AD3 applied to the input port Pin. Upon detection of the voltages AD2 and AD3, a judgment process (S40) is executed to determine which detected voltage is to be used for providing the humidity by comparing the voltage AD2 with the threshold value, e.g., 1.5 volts. As such, depending upon the value of the detection voltage AD2, used is either the first humidity detecting characteristic as shown in FIG. 3 and provided by the first humidity detection serially connected circuit 52A or the second humidity detecting characteristic as shown in FIG. 4 and provided by the second humidity detection serially connected circuit 52B whichever is appropriate. In other words, the humidity sensor 54 uses two different characteristics that provide different humidity values corresponding to the detected voltage (or resistance). As such, the above-described embodiment can broaden a dynamic range (detection resolution) in the detection voltages in a low-temperature/low-humidity range and high-temperature/high-humidity range, for example. Consequently, detection of the humidity with high accuracy can be accomplished.

In the above-described embodiment, the humidity is finally provided based either on the detection voltage AD2 if the latter is equal to or larger than the threshold value (e.g., 1.5 volts) or on the detection voltage AD3 if the latter is smaller than the threshold value. In this way, one of the voltages AD2 and AD3 detected following the first and second humidity detecting characteristics, respectively, is selectively used, so that the resolution of the detected voltages can be increased. As a result, the detection accuracy of the humidity sensor 54 can be improved over an entire detectable range from a low-temperature/low-humidity point to the high-temperature/high-humidity point.

Although the present invention has been described with respect to a specific embodiment, it will be appreciated by one skilled in the art that a variety of changes and modifications may be made without departing from the scope of the invention.

For example, in the above-described embodiment, while the detection voltage AD2 obtained in the first humidity detecting mode (S20) is compared with the threshold value Vth to determine which detection voltage AD2 or AD3 is used (S40) and the humidity is finally obtained based on the selected voltage. The invention is not limited to the above-described procedure. Instead, the detection voltage AD3 obtained through the second humidity detecting mode (S30) may be compared with the threshold value Vth. Either the detection voltage AD2 or the detection voltage AD3 may be selected based on the comparison results and the humidity may be provided based on the selected detection voltage AD2 or AD3. When the detection voltage AD3 is larger than the threshold value Vth, the humidity detection is performed using the detection voltage AD2 whereas when the detection voltage AD3 is equal to or smaller than the threshold value Vth, the humidity detection is performed using the detection voltage AD3. Such procedure can also improve the detection resolution similar to the above-described embodiment. As a result, the detection accuracy of the humidity sensor 54 can be improved over an entire detectable range from a low-temperature/low-humidity point to the high-temperature/high-humidity point.

In the above-described embodiment, the first humidity detecting mode (S20) and the second humidity detecting mode (S30) are executed and then the processes in S40 onward are executed in the humidity detecting process. The invention is not limited to such a procedure. Instead, only the temperature detecting mode (S10 and the first humidity detecting mode (S20) may be executed and the processes in S40 onward may be dispensed with, if the detection accuracy in the low-temperature/low-humidity range or high-temperature/high-humidity range is not so important. Alternatively, only the temperature detecting mode (S10) and the second humidity detecting mode (S30) may be executed but other processes may be dispensed with.

In the above-described modifications, the humidity sensor having a temperature-dependent resistance characteristic uses the resistance versus humidity characteristic in relation to the temperature or the detection voltage AD1 detected by the thermistor and also uses the detection voltage AD2 or AD3 obtained through the second detecting process using the resistance of the humidity sensor. Accordingly, the detection accuracy of the humidity sensor can be improved. In the above instances, either one of the first and second humidity detection tables 65A and 65B can be dispensed with.

Although the above-described embodiment describes the sensor device provided in the device having a printing function, the present invention is not only applicable thereto but applicable to, for example, a multi-function peripheral having at least one of printing function, scanner function, copying function, facsimile transmission/reception function and so on. The device to which the invention is applicable may not be provided with the printing function. The sensor device according to the invention is applicable to various kinds of devices which perform various kinds of adjustments based on measured results of various parameters including temperature and humidity.

While the above-described embodiment uses the thermistor and humidity sensor as examples of resistance change type sensors, the invention is not limited to the use of such specific devices. Other resistance change type sensors, such as distortion gauge, volume sensor, CdS cell illumination sensor, may be employed to detect parameters other than the humidity. In other words, the sensor device according to the invention is not limited to those for detecting temperature and humidity.

The above-described embodiment exemplifies a printer 1 having a single ASIC 60 as an example of a controller and a single CPU 62 contained in the ASIC 60 executes various processes. The invention is not limited to use the single ASIC but may use a plurality of CPUs and/or ASICs to execute the required processes. Further, the controller may not be configured from the ASIC having the CPU 62 by may be configured by a CPU and a plurality of peripheral circuits connected thereto.

What is claimed is:

1. A sensor device comprising:
    a first resistance change sensor having a first terminal and a second terminal and configured to detect a first parameter;
    a second resistance change sensor having a third terminal and a fourth terminal connected to the first terminal and configured to detect a second parameter different from the first parameter;
    a fixed resistor having a fifth terminal and a sixth terminal connected to both the first terminal and the fourth terminal; and
    a controller having a first output port connected to the second terminal, a second output port connected to the third terminal, a third output port connected to the fifth terminal, and an input port connected to all of the first terminal, the fourth terminal and the sixth terminal, the controller being configured to:
        execute a first signal applying process wherein the first output port is rendered high impedance, and an alternating voltage is applied across the second output port and the third output port where the alternating voltage alternately changes between a first voltage level and a second voltage level different from the first voltage level, the high impedance being high to substantially be equivalent to an open circuit, execute a first detection process wherein a first detection voltage applied to the input port is detected when the second output port is at one of the first voltage level and the second voltage level and the third output port is at remaining one of the first voltage level and the second voltage level during execution of the first signal applying process, execute a second signal applying process subsequent to the execution of the first detection process, wherein one of the second output port and the third output port is rendered the high impedance, the alternating voltage is applied across the first output port and remaining one of the second output port and the third output port, execute a second detection process subsequent to the execution of the first detection process, wherein a second detection voltage applied to the input port is detected when the first output port is at one of the first voltage level and the second voltage level and the second output port or third output port whichever is not rendered the high impedance is at remaining one of the first voltage level and the second voltage level during execution of the second signal applying process, and execute a parameter detection process wherein a value of the first parameter is determined using the first detection voltage and the second detection voltage.

2. The sensing device according to claim 1, further comprising a memory storing a table containing a plurality of sets of data, each set of data containing a first value equivalent to the first detection voltage, a second value equivalent to the second detection voltage and a humidity value, the first value, the second value and the humidity value in each set being correlated to one another.

3. The sensor device according to claim 1,
wherein the first resistance change sensor is configured to be driven by an alternating signal and detect humidity, the first resistance change sensor having temperature-dependent resistance-versus-humidity characteristics,
wherein the second resistance change sensor comprises a thermistor, and
wherein in the parameter detection process, the controller is configured to determine a value of humidity using a resistance-versus-humidity characteristic corresponding to the first detection voltage related to a temperature detected in the first detection process, and also using the second detection voltage related to humidity detected in the second detection process.

4. The sensor device according to claim 3,
wherein in the second signal applying process, the controller is configured to:
render the third output port the high impedance, apply the alternating voltage across the first output port and the second output port, and detect the second detection voltage applied to the input port as a first humidity indicating voltage, and
render the second output port the high impedance, apply the alternating voltage across the first output port and the third output port, and detect the second detection voltage applied to the input port as a second humidity indicating voltage, and
wherein the controller is further configured to execute a judgment process wherein judgment is made as to which of the first humidity indicating voltage and the second humidity indicating voltage is relevant to use in determining the value of humidity upon comparison of the second humidity indicating voltage with a threshold voltage.

5. The sensor device according to claim 3,
wherein in the second signal applying process, the controller is configured to:
render the third output port the high impedance, apply the alternating voltage across the first output port and the second output port and detect the second detection voltage applied to the input port as a first humidity indicating voltage, and
render the second output port the high impedance, apply the output voltage across the first output port and the third output port and detect the second detection voltage applied to the input port as a second humidity indicating voltage, and
wherein the controller is further configured to execute a judgment process wherein judgment is made to determine which of the first humidity indicating voltage and the second humidity indicating voltage is relevant to use as a basis for outputting the humidity upon comparison of the first humidity indicating voltage with a threshold voltage.

6. The sensor device according to claim 5,
wherein the first resistance change sensor operates as a humidity sensor, the humidity sensor having a resistance characteristic such that resistance of the humidity sensor decreases as humidity increases, and the thermistor has a resistance characteristic such that resistance of the thermistor decreases as temperature increases, and
wherein the controller is further configured to:
detect the first humidity indicating voltage under a condition where the first output port is at the first voltage level and the second output port is at the second voltage level lower than the first voltage level,
perform humidity detection using the first humidity indicating voltage when the first humidity indicating voltage is greater than the threshold voltage, and
perform humidity detection using the second humidity indicating voltage when the first humidity indicating voltage is equal to or smaller than the threshold voltage.

7. The sensor device according to claim 5,
wherein the first resistance change sensor operates as a humidity sensor, the humidity sensor having a resistance characteristic such that resistance of the humidity sensor decreases as humidity increases, and
wherein the controller is further configured to:
detect the second humidity indicating voltage under a condition where the first output port is at the first voltage level and the third output port is at the second voltage level lower than the first voltage level,
perform humidity detection using the first humidity indicating voltage when the second humidity indicating voltage is greater than the threshold voltage, and
perform humidity detection using the second humidity indicating voltage when the first humidity indicating voltage is equal to or smaller than the threshold voltage.

8. An image forming device comprising:
a sensor device; and
an image forming portion configured to form an image on an object based on image data,
wherein the sensor device includes:

a first resistance change sensor having a first terminal and a second terminal and configured to detect a first parameter;

a second resistance change sensor having a third terminal and a fourth terminal connected to the first terminal and configured to detect a second parameter different from the first parameter;

a fixed resistor having a fifth terminal and a sixth terminal connected to both the first terminal and the fourth terminal; and a controller having a first output port connected to the second terminal, a second output port connected to the third terminal, a third output port connected to the fifth terminal, and an input port connected to all of the first terminal, the fourth terminal and the sixth terminal, the controller being configured to:

execute a first signal applying process wherein the first output port is rendered high impedance, and an alternating voltage is applied across the second output port and the third output port where the alternating voltage alternately changes between a first voltage level and a second voltage level different from the first voltage level, the high impedance being high to substantially be equivalent to an open circuit, execute a first detection process wherein a first detection voltage applied to the input port is detected when the second output port is at one of the first voltage level and the second voltage level and the third output port is at remaining one of the first voltage level and the second voltage level during execution of the first signal applying process, execute a second signal applying process subsequent to the execution of the first detection process, wherein one of the second output port and the third output port is rendered the high impedance, the alternating voltage is applied across the first output port and remaining one of the second output port and the third output port, execute a second detection process subsequent to the execution of the first detection process, wherein a second detection voltage applied to the input port is detected when the first output port is at one of the first voltage level and the second voltage level and the second output port or third output port whichever is not rendered the high impedance is at remaining one of the first voltage level and the second voltage level during execution of the second signal applying process, and execute a parameter detection process wherein a value of the first parameter is determined using the first detection voltage and the second detection voltage.

9. The image forming device according to claim 8, wherein the sensor device further comprises a memory storing a table containing a plurality of sets of data, each set of data containing a first value equivalent to the first detection voltage, a second value equivalent to the second detection voltage and a humidity value, the first value, the second value and the humidity value in each set being correlated to one another.

10. The image forming device according to claim 8, wherein the first resistance change sensor is configured to be driven by an alternating signal and detect humidity, the first resistance change sensor having temperature-dependent resistance-versus-humidity characteristics, wherein the second resistance change sensor comprises a thermistor, and wherein in the parameter detection process, the controller is configured to determine a value of humidity using a resistance-versus-humidity characteristic corresponding to the first detection voltage related to a temperature detected in the first detection process, and also using the second detection voltage related to humidity detected in the second detection process.

11. The image forming device according to claim 10, wherein in the second signal applying process, the controller is configured to:

render the third output port the high impedance, apply the alternating voltage across the first output port and the second output port, and detect the second detection voltage applied to the input port as a first humidity indicating voltage, and render the second output port the high impedance, apply the alternating voltage across the first output port and the third output port, and detect the second detection voltage applied to the input port as a second humidity indicating voltage, and wherein the controller is further configured to:

execute a judgment process wherein judgment is made as to which of the first humidity indicating voltage and the second humidity indicating voltage is relevant to use in determining the value of humidity upon comparison of the second humidity indicating voltage with a threshold voltage.

12. The image forming device according to claim 10, wherein in the second signal applying process, the controller is configured to:

render the third output port the high impedance, apply the alternating voltage across the first output port and the second output port and detect the second detection voltage applied to the input port as a first humidity indicating voltage, and render the second output port the high impedance, apply the output voltage across the first output port and the third output port and detect the second detection voltage applied to the input port as a second humidity indicating voltage, and wherein the controller is further configured to execute a judgment process wherein judgment is made to determine which of the first humidity indicating voltage and the second humidity indicating voltage is relevant to use as a basis for outputting the humidity upon comparison of the first humidity indicating voltage with a threshold voltage.

13. The image forming device according to claim 12, wherein the first resistance change type-sensor operates as a humidity sensor, the humidity sensor having a resistance characteristic such that resistance of the humidity sensor decreases as humidity increases, and the thermistor has a resistance characteristic such that resistance of the thermistor decreases as temperature increases, and wherein the controller is further configured to:

detect the first humidity indicating voltage under a condition where the first output port is at the first voltage level and the second output port is at the second voltage level lower than the first voltage level, perform humidity detection using the first humidity indicating voltage when the first humidity indicating voltage is greater than the threshold voltage, and perform humidity detection using the second humidity indicating voltage when the first humidity indicating voltage is equal to or smaller than the threshold voltage.

14. The image forming device according to claim 12, wherein the first resistance change sensor operates as a humidity sensor, the humidity sensor having a resistance characteristic such that resistance of the humidity sensor decreases as humidity increases, and wherein the controller is further configured to:
- detect the second humidity indicating voltage under a condition where the first output port is at the first voltage level and the third output port is at the second voltage level lower than the first voltage level,
- perform humidity detection using the first humidity indicating voltage when the second humidity indicating voltage is greater than the threshold voltage, and
- perform humidity detection using the second humidity indicating voltage when the first humidity indicating voltage is equal to or smaller than the threshold voltage.

\* \* \* \* \*

UNITED STATES PATENT AND TRADEMARK OFFICE
CERTIFICATE OF CORRECTION

PATENT NO. : 9,753,430 B2  
APPLICATION NO. : 14/224223  
DATED : September 5, 2017  
INVENTOR(S) : Jie Zheng et al.

Page 1 of 1

It is certified that error appears in the above-identified patent and that said Letters Patent is hereby corrected as shown below:

In Column 18, Claim 13, Line 52:
Please delete "change type-sensor operates" and insert --change sensor operates--

Signed and Sealed this
Nineteenth Day of June, 2018

Andrei Iancu
*Director of the United States Patent and Trademark Office*